(12) United States Patent
van Erp et al.

(10) Patent No.: US 9,737,729 B2
(45) Date of Patent: Aug. 22, 2017

(54) MODULAR APPLICATOR FOR BRACHYTHERAPY

(71) Applicant: Nucletron Operations B.V., Veenendaal (NL)

(72) Inventors: Wilhelmus Petrus Martinus Maria van Erp, Veenendaal (NL); Tommy Robert Oscar Martens, Veenendaal (NL); Gaetan Stephan Marie van Wijck, Veenendaal (NL); Cor van de Wardt, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 345 days.

(21) Appl. No.: 14/063,408

(22) Filed: Oct. 25, 2013

(65) Prior Publication Data

US 2014/0121443 A1 May 1, 2014

Related U.S. Application Data (60) Provisional application No. 61/718,410, filed on Oct. 25, 2012.

(30) Foreign Application Priority Data

Oct. 25, 2012 (NL) ...................... 2009699

(51) Int. Cl.
*A61N 5/10* (2006.01)

(52) U.S. Cl.
CPC ......... *A61N 5/1007* (2013.01); *A61N 5/1016* (2013.01); *A61N 2005/1003* (2013.01)

(58) Field of Classification Search
CPC .......... A61N 5/1016; A61N 2005/1003; A61N 5/1007
See application file for complete search history.

(56) References Cited

U.S. PATENT DOCUMENTS

| | | | | |
|---|---|---|---|---|
| 5,863,284 A | * | 1/1999 | Klein | A61N 5/1002 600/3 |
| 5,947,891 A | * | 9/1999 | Morrison | A61N 5/1016 600/6 |
| 7,497,820 B2 | * | 3/2009 | White | A61N 5/1015 600/3 |
| 2011/0257459 A1 | | 10/2011 | Sutton et al. | |

* cited by examiner

*Primary Examiner* — Christine H Matthews
(74) *Attorney, Agent, or Firm* — Bookoff McAndrews, PLLC (57) ABSTRACT

Embodiments of the present disclosure relate to a modular applicator for enabling a brachytherapy treatment, comprising a central core and an outer sleeve, wherein the central core is adapted with a fixation mechanism for affixing the outer sleeve to the central core, wherein the outer sleeve is manufactured from a substantially rigid or shapeable material.

35 Claims, 5 Drawing Sheets

MODULAR APPLICATOR FOR BRACHYTHERAPY

PRIORITY

This patent application claims the benefit of priority under 35 U.S.C. §120 to U.S. Provisional Application No. 61/718,410, filed on Oct. 25, 2012, the entirety of which is incorporated herein by reference. This patent application also claims the benefit of priority under 35 U.S.C. §119 to The Netherlands Patent Application No. 2009699, filed on Oct. 25, 2012, which is incorporated herein by reference in its entirety.

FIELD OF THE INVENTION

The invention relates to a modular applicator for brachytherapy.

BACKGROUND OF THE INVENTION

Cancers, having increased incidence rate in the last decade of the 20$^{th}$ century, require substantial effort from medical professionals in terms of early diagnosis, logistics and availability of suitable treatment. However, it is appreciated that over 1.3 million new (skin) cancers are diagnosed annually and are increasing at a rate of about 5% per year.

Non proliferated cancers, being substantially superficial lesions, may be treated in different ways. First, surgery may be envisaged. However, such technique may be disadvantageous in terms of long waiting lists and complications related to post-treatment care. In addition, due to invasive character of surgery contamination of the wound by infections may present an additional risk. Secondly, external irradiation using electrons or electromagnetic radiation may be envisaged. Such techniques have a disadvantage that the patient has to receive about 25-30 fractions, which may be complicated for less mobile patients. In addition, irradiation of healthy tissues as well as reproducibility of the external beams with respect to the movable target may be a challenge.

Brachytherapy may provide an attractive compromise, wherein the radioactive sources are delivered inside the patient using applicators, either interstitially or intracavitary. Usually, a medical professional employs a standard applicator for treating different patients. However, due to difference in local anatomies the standard applicator may be not always an optimal solution for matching the patient geometry and for providing a pre-planned dose distribution inside the patient. Embodiments of the standard applicators are known from Nucletron, Applicator guide, Company Brochure, 2011.

Recently, it has been attempted to provide a customizable applicator, which may be composed of modules. An embodiment of a modular applicator is known from US 2011/0257459. In the known modular applicator a stack of longitudinal segments is provided, wherein the segments may be coupled to each other using suitable cooperating surfaces. Each segment is provided with a plurality of passages for providing a set of customizable channels for insertion of a radioactive source. A tip of the stack of segments may comprise one or more alignment notches, which may help define a certain orientation between the tip and a distal stacking component.

It is a disadvantage of the known modular applicator that it may insufficiently provides a desired variability of the resulting applicator in terms of shapes and dimensions.

SUMMARY OF THE INVENTION

It is an object of the invention to provide an improved modular applicator for brachytherapy which is capable of enabling a higher variability of shapes and dimensions in use.

To this end the modular applicator for enabling a brachytherapy treatment according to an aspect of the invention comprises a central core and an outer sleeve, wherein the central core is adapted with a fixation mechanism for affixing the outer sleeve to the central core, wherein the outer sleeve is manufactured from a substantially rigid or shapeable material.

It is found that a substantial improvement of the applicator's handling may be achieved when the applicator comprises a core and an outer sleeve mountable on it. The core may be fully rigid, or, alternatively, it may be partially rigid. In the latter case the core may comprise portions which are shapeable or elastic. This has an advantage that the procedure of arrangement of the sleeve on the core may be relaxed for the medical specialist. Next, it is found that the modular applicator comprising the core and the sleeve is particularly advantageous when an elongated, peer-shaped dose distribution pattern is required. This may be achieved because a substantially continuous core and the substantially continuous sleeve contribute to an improvement of the dose distribution around the applicator. For example, for a gynecological applicator the core may be mounted on an intrauterine tube. Preferably, the cross-sectional dimension (diameter) of the core is 0.6 cm. However, it is found that when the core has dimensions in the range of about 0.5-5 cm, an improved mechanical balance and stability for the sleeve on the core.

Further, in a particular embodiment, the sleeve and/or the core are provided with a fixation mechanism which may enable easy mounting of the sleeve on the core. For example, a click-on fixation, such as a snap fit arrangement may be envisaged. Alternatively, a bayonet fixation may be provided. Those skilled in the art would readily appreciate which modifications or other easy and fast fixation mechanisms may be used for affixing the sleeve on the core. Still alternatively, a fixation ring may be provided to at least partially embrace the sleeve to press the sleeve against the core. The fixation ring may be manufactured from an elastic material. In these ways a one-hand handling of the applicator by a medical professional may be enabled, which is advantageous for clinical practice.

Next, in a particular embodiment of the applicator according to an aspect of the invention the dimensions of the core and/or the dimensions of the sleeve may be suitably customized on demand. This feature is further discussed below.

Further, it is found that a sleeve cooperating with the core provides a highly ergonomic device, which has a higher acceptance by the patients. In particular the latter considerations are valid for intracavitary brachytherapy, such as vaginal applications.

The core may be substantially cylindrically shaped, or, alternatively, it may have an arbitrary non-cylindrical shape. More in particular, the core may be shapeable in use.

Preferably, the fixation mechanism comprises a snap fit arrangement or a rotational fit arrangement to affix the sleeve to the core of the applicator according to the invention.

Although it will be appreciated that the applicator may be customizable by suitably selecting an appropriate sleeve, for example from a set of available sleeves, it is also possible that the sleeve itself is shapeable. In particular, the sleeve may be at least partially manufactured from a settable material, such as a per se known settable foam. More details on this embodiment will be presented with reference to FIGS. 1a and 1b.

In a particular embodiment of the applicator according to a further aspect of the invention at least a portion of the outer surface of the sleeve is irregular. For example, at least the portion of the outer surface may comprise a set of local depletions or bumps for providing local areas of under pressure. These local areas of under pressure may have a higher affinity to affix to a surrounding tissue. It is found that when the applicator is provided with an irregular surface (having bumps, projections, depletions or slots) it may be reliably maintained within a suitable cavity, such as vagina or rectum due to interaction of the patient's tissues with the irregular surface.

In a further particular embodiment of the application, the sleeve is transparent. This feature is found to be particularly useful for enabling reliable handling and mounting of the applicator. Still preferably, the applicator is provided with a suitable plurality of customized sleeves. For example, the sleeves may have different longitudinal or cross-sectional dimensions.

In a still further embodiment, the customized sleeves are adapted to be manufactured in vivo. For example, the sleeves may be manufactured from a shapeable material, such as foam, settable polymer, or the like. For example, an outer surface of the sleeve may be manufactured from a settable polymer which is adapted to be set at about 37 degrees Celsius. Alternatively, the outer surface of the applicator may comprise a material which may be set to comply to an external shape. For example, the outer surface of the applicator may comprise a vacuum bag filled with particles. Under evacuation of the bag, the particles come together and the applicator becomes substantially rigid, while matching the surface of the patient abutting the applicator.

Preferably, at least a proximal portion of the customized sleeves is shapeable. This feature is found to be particularly advantageous for customizing the form and shape of the ovoids used with the gynecological applicator. It will be appreciated that in accordance with the aspect of the invention the ovoids are mimicked by the shape of the sleeve and are no longer a separate item which needs to be affixed to the intra-uterine tube.

In a still further particular embodiment of the modular applicator, the proximal portion of the sleeve is provided with sub-portions capable of lateral displacement with respect to each other. This embodiment is discussed in more detail with reference to FIGS. 4a.

It is found to be particularly advantageous to provide an indicator for indicating or quantifying the value of displacement of the sub-portions of the proximal portion of the applicator. This feature is discussed with more detail with reference to FIG. 4b.

In a still further embodiment of the applicator according to a further aspect of the invention, the sleeve is modular.

This technical measure is based on the insight that it may be further simplified to customize the shape and the dimension of the applicator, when the applicator is built from segments. It will be appreciated that a great plurality of embodiments is possible. For example, the core and the sleeve may both comprise segments, such as longitudinal, cross-sectional or sector segments. This embodiment is explained in more detail with reference to FIG. 5.

In a still further embodiment of the applicator according to a still further aspect of the invention the cross-section of the sleeve is modulated along the longitudinal direction of the sleeve.

This technical measure is based on the insight that by allowing the sleeve to have different cross-sectional dimensions across its length an improved anatomical match between the applicator and the patient may be achieved. This embodiment is discussed in more detail with reference to FIG. 6.

These and other aspects of the invention will be discussed with reference to drawings wherein like reference numerals or signs relate to like elements. It will be appreciated that the drawings are presented for illustration purposes only and may not be used for limiting the scope of the appended claims.

DETAILED DESCRIPTION OF THE DRAWINGS

Figure 1A:
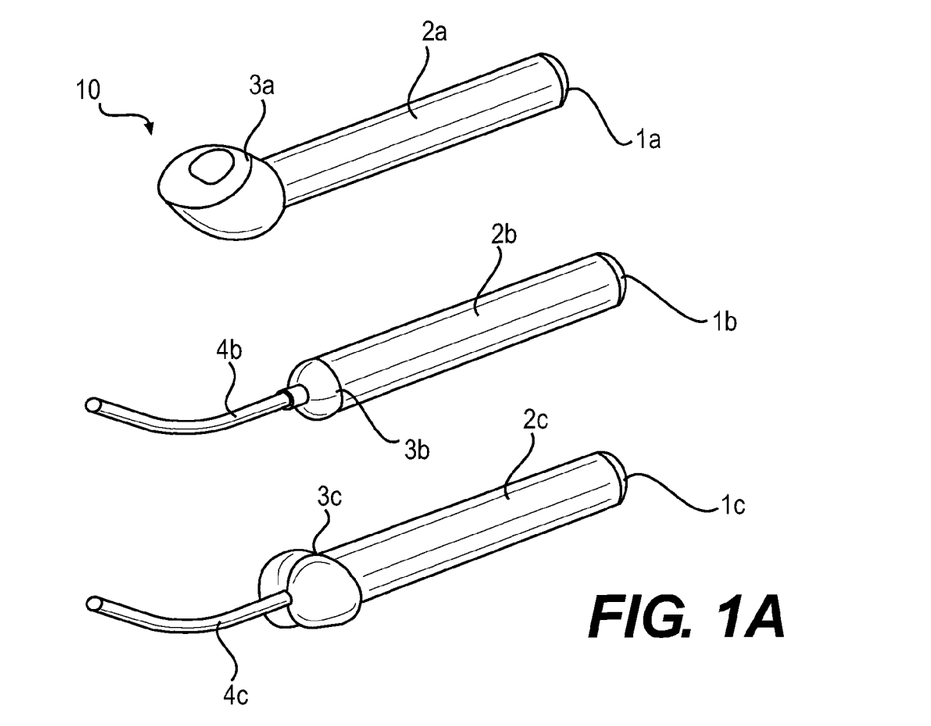
FIG. 1a presents in a schematic way an embodiment of the modular applicator.

FIG. 1a presents in a schematic way an embodiment of the modular applicator. In the upper view, a configuration is shown wherein a cylindrical central core 1a is used to accommodate an outer sleeve 2a, which is also substantially cylindrical. The outer sleeve 2a is adapted with a specifically formed distal portion 3a, which forms part of the dose delivery configuration.

In this way a known applicator comprising a plurality of components, such as a central catheter, a ring applicator and so on is replaced by a modular applicator having a central core and an outer sleeve which may be custom made.

The middle view shows schematically a further embodiment of the modular applicator, wherein the central core 1b is adapted to accommodate a cylindrical sleeve 2b having a distal portion 3b approximating ovoids by shape. In addition, the central core is supporting the intra-uterine tube 4b. The dimension of the distal portion of the sleeve may be modified in use.

Also this embodiment has an advantage that handling and assembling of the complicated applicator geometry is simplified.

The lower view presents schematically an embodiment of the modular applicator wherein the dimension of the distal portion is modified in use. This feature has an advantage in that the distal portion of the sleeve is capable of mimicking different dimensions of the ovoids. Accordingly, the modular applicator comprises the central core 1c, the cylindrical sleeve 2c and the ovoid portion 3c, which may be tuned in use. Finally, the modular applicator may comprise an inter-uterine tube 4c. More details on this embodiment will be given with reference to FIG. 1b.

Figure 1B:
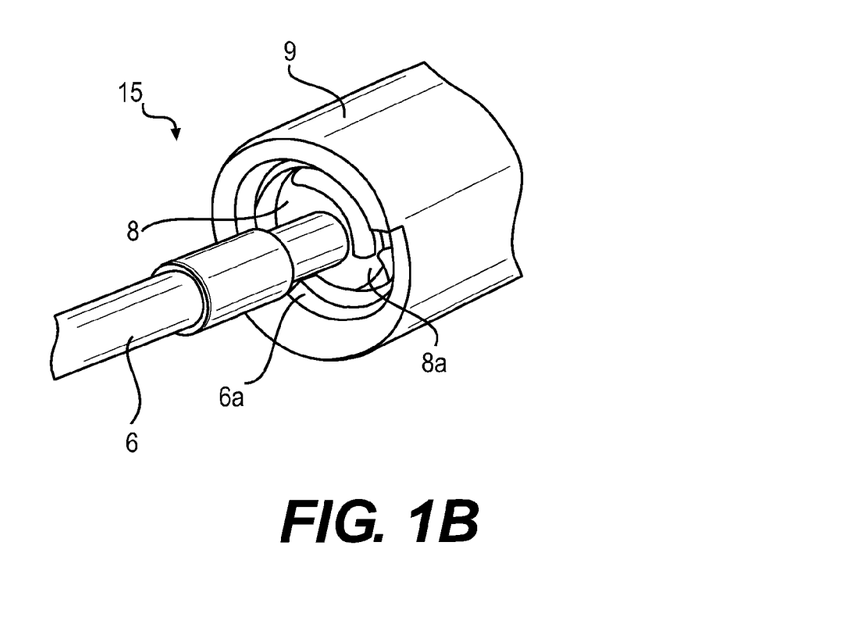
FIG. 1b presents in a schematic way an embodiment of a rotation mechanism for enabling displacement of the distal portion of the sleeve.

FIG. 1b presents in a schematic way an embodiment of a rotation mechanism for enabling displacement of the distal portion of the sleeve. Accordingly, the modular applicator 15 comprises a central core 8 and a cylindrical sleeve 9 which is affixed to the central core using a fixation mechanism (not shown). Various embodiments of the fixation mechanism are envisaged, such as, a snap fit, a lock, fastening clamp and so on.

In order to change a dimension of the distal portion of the modular applicator, it is provided with an actuator 8a, such as a threading, which may be actuated by a used. By rotating the actuator 8a, the distal portion of the sleeve may be urged to increase its cross-section. It will be appreciated that the rotating actuator 8a is an embodiment of a rotational fit arrangement, discussed with reference to the foregoing.

In order to connect the modular applicator to a suitable afterloading device, it comprises a port 6a connectable to the source guide 6.

Figure 2:
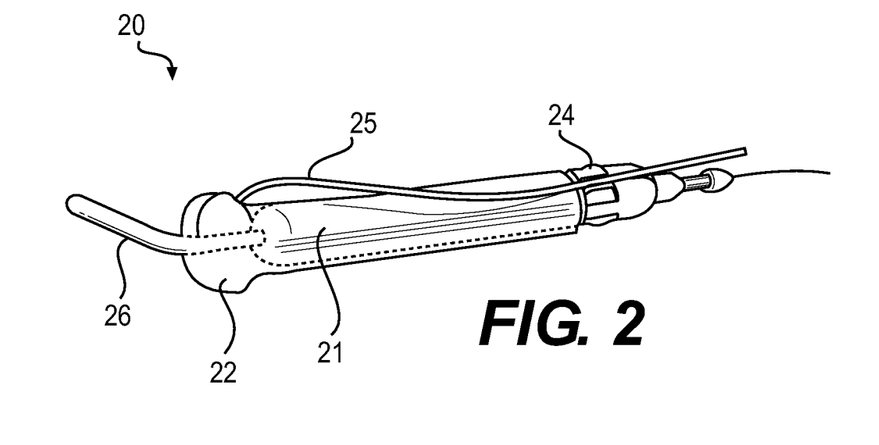
FIG. 2 presents in a schematic way an embodiment of the applicator having a transparent sleeve.

FIG. 2 presents in a schematic way an embodiment of the applicator 20 having a transparent sleeve. Accordingly, the modular applicator comprises a central core 21 on which a transparent sleeve 22 is mounted. This embodiment has an advantage that the inner structures of the applicator may be inspected during assembly. The modular applicator 20 further comprises a suitable set of flexible catheters 25, an actuator 24 for altering a dimension of the distal portion 22 and an inter-uterine tube 26.

Figure 3:
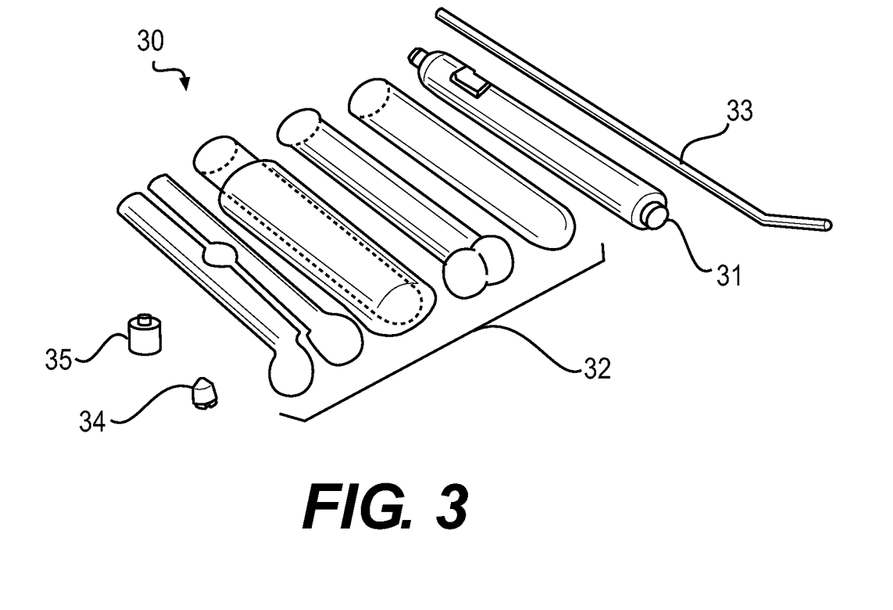
FIG. 3 presents in a schematic way an embodiment of the applicator having a set of inter-changeable sleeves.

FIG. 3 presents in a schematic way an embodiment of the applicator 30 having a set of inter-changeable sleeves 32. The central core 31 is suitably provided with a conduit for allowing passage of the inter-uterine tube 33 there through. The central core 31 is further provided with a fixation mechanism (not shown) for affixing and retaining the outer sleeve on the central core. Preferably, the fixation mechanism comprises a snap fit arrangement or a rotational fit arrangement. The modular applicator may further comprise a catheter cap 34 and a fixation nut 35 for affixing catheters or source guides to the applicator.

Figure 4A:
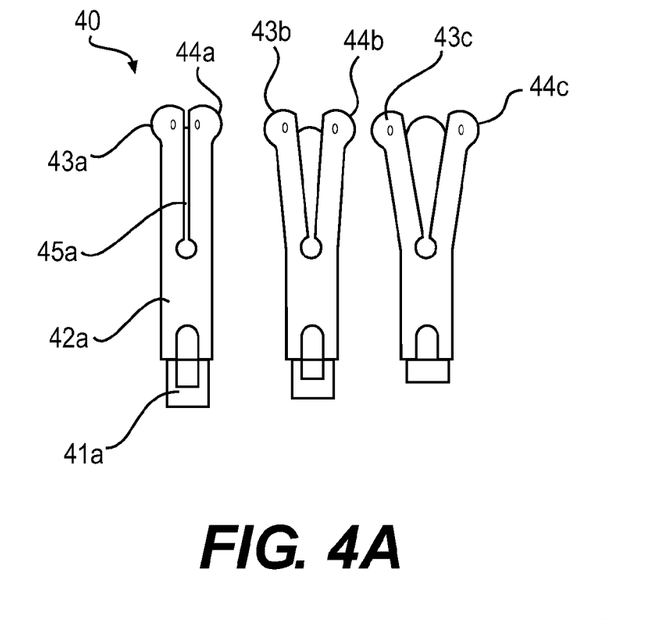
FIG. 4a presents in a schematic way an embodiment of the applicator having a sleeve comprising pivotable portions.

FIG. 4a presents in a schematic way an embodiment of the applicator having a sleeve comprising pivotable portions. The modular applicator 40 comprises a central core 41a and an outer sleeve 42a, mounted on the central core. The outer sleeve is provided with a slit 45a separating the distal portion of the sleeve in two parts 43a, 44a. By using an actuator (not shown) it is possible to displace the distal portions 43a, 44a away from each other, see embodiments 43b, 44b and 43c, 44c.

It will be appreciated that this embodiment provides for an increased flexibility in matching the patient anatomy for dose delivery. Because the distal portion may contribute to the dose delivery by accommodating one or more radioactive sources, it is found to be useful to allow for different spreads in the distal portion of the sleeve, thereby mimicking different ovoid geometries and configurations.

Figure 4B:
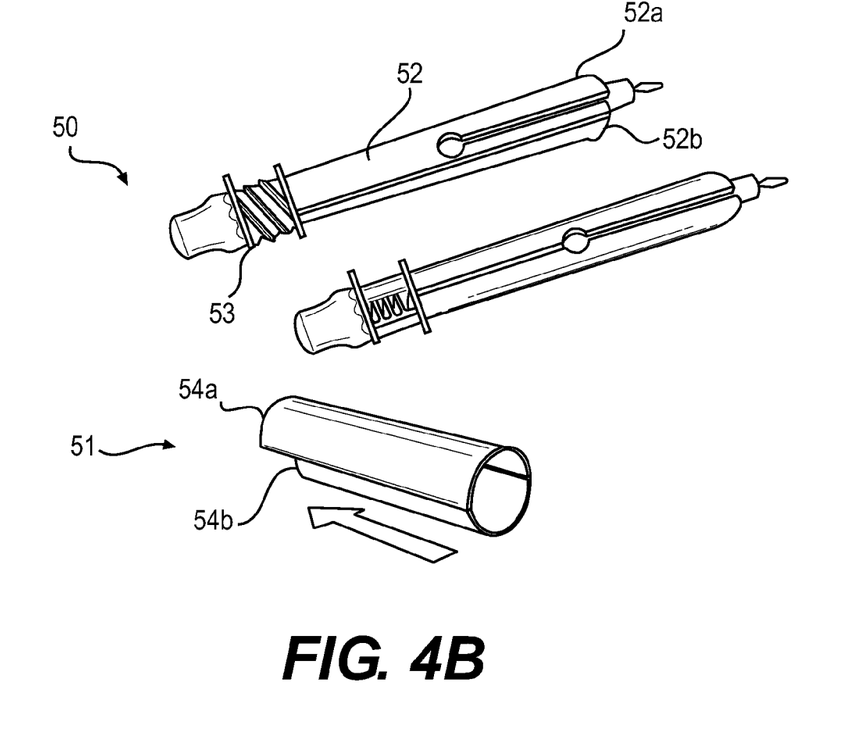
FIG. 4b presents in a schematic way a further embodiment of the applicator having pivotable portions.

FIG. 4b presents in a schematic way a further embodiment of the applicator having pivotable portions. In this embodiment of the modular applicator 50, it is provided with a threaded actuator and the sleeve having two semi-cylindrical halves. The sleeve 52 is similar to the embodiment shown with reference to FIG. 4a, i.e. it is provided with a slit separating two halves 52a, 52b of the distal portion of the sleeve. In order to urge the halves 52a, 52b away from each other, the modular applicator 50 is provided with a threaded actuator 53. By rotating the sleeve with respect to the thread 53 the halves 52a, 52b are urged away from each other. It will be appreciated that the distal portion of the sleeve may be divided in any suitable number of portions, 2, 3, 4, etc.

In view 51 a still further embodiment of the sleeve is schematically presented. The sleeve comprises two slidable parts 54a, 54b. This embodiment is found to be advantageous for simplifying assembly of the modular applicator.

Figure 5:
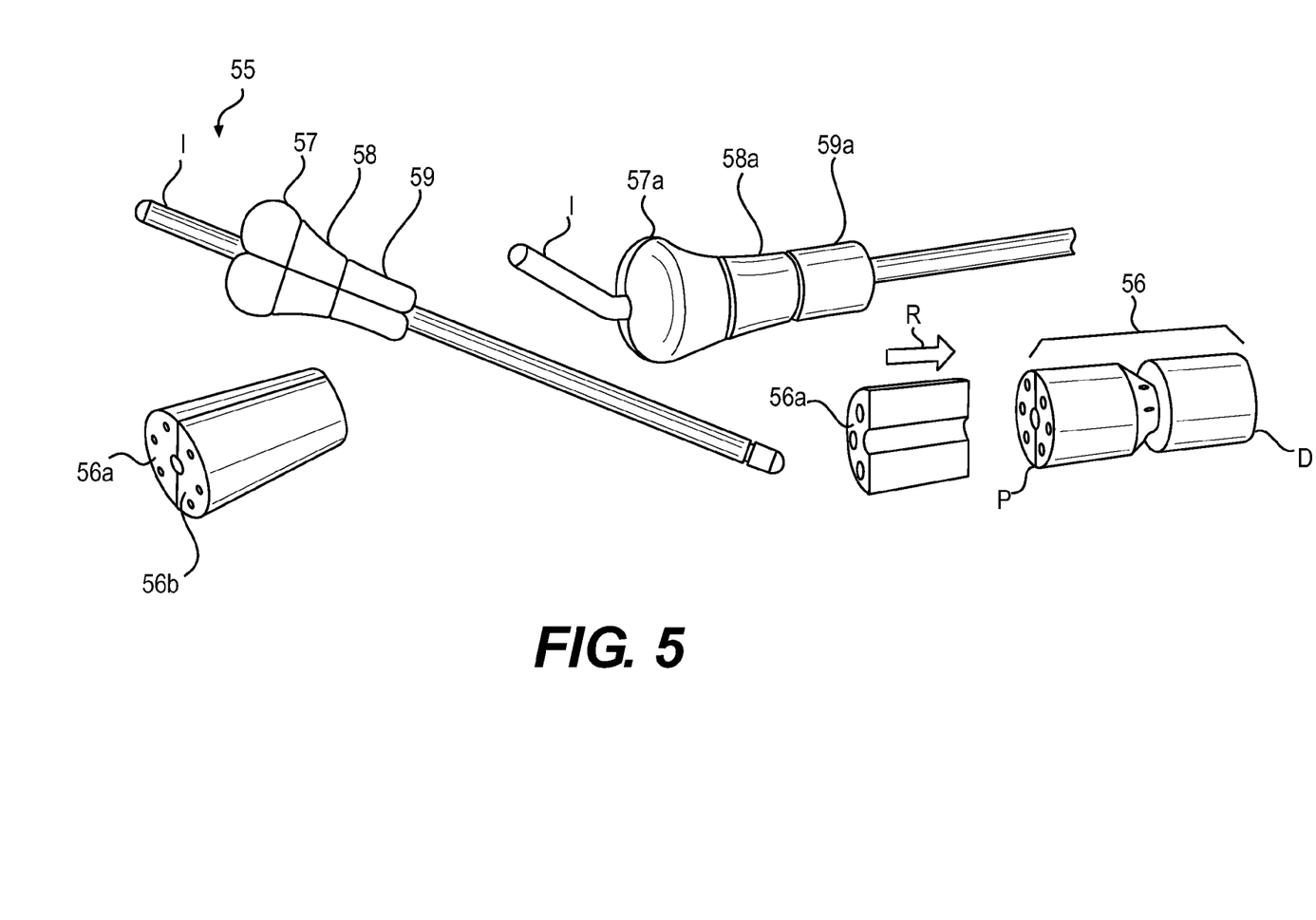
FIG. 5 presents in a schematic way an embodiment of the applicator having a segmented sleeve.

FIG. 5 presents in a schematic way an embodiment of the applicator having a segmented sleeve. The modular applicator may be divided into suitable segments—longitudinal or cross-sectional, see segments 57, 58, 59, 57a, 58a, 59a. It will be appreciated that a set of suitable segments may be provided having segments of different configuration and different dimensions. Accordingly, by assembling the sleeve the dimensions and the configuration of the segments may be selected to match the patient anatomy and the dose plan.

The segments 57, 58, 59, 57a, 58a, 59a are provided on a core (not shown), which may also be provided in segments. The core has a through opening for allowing passage of the intra-uterine tube I.

Alternatively, the sleeve may comprise two longitudinal segments 56a, 56b, which may be to stacked to form the outer sleeve 56 by displacing them along a direction R. Preferably, first the distal portion of the applicator is stacked, after which the proximal portion P may be assembled and connected to a suitable afterloading device (not shown).

Figure 6:
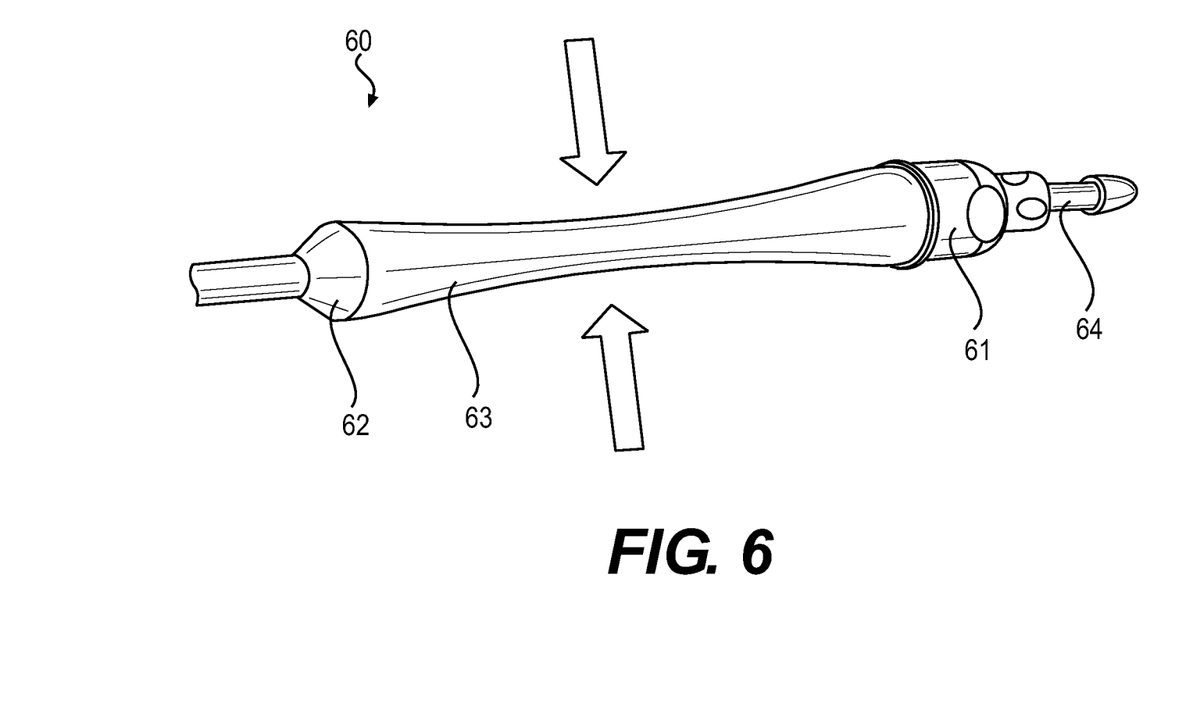
FIG. 6 presents in a schematic way an embodiment of the applicator having a modulated cross-section.

FIG. 6 presents in a schematic way an embodiment of the applicator having a modulated cross-section. The modular applicator 60 comprises a central core 61 connectable to a suitable afterloading device by means of a port 64. A sleeve 62 is assembled on the central core 61 using a suitable fixation mechanism (not shown). In accordance with the present aspect of the invention, the cross-sectional dimension of the sleeve is modulated along the longitudinal direction of the sleeve. For instance, a region 63 may be provided having the smallest cross-section. However, any modulation of the thickness may be envisaged.

It will be further appreciated that the thickness modulation may be pre-set, i.e. the outer sleeve may be pre-fabricated having a pre-determined curvature of the outer surface. Alternatively, the outer surface of the sleeve may be manufactured from a shapeable material, such as foam, settable polymer, vacuum shapeable material, or the like. In this case, the local dimension of the sleeve may be set in use, which has an advantage of the increased versatility and patient anatomy fit.

While specific embodiments have been described above, it will be appreciated that the invention may be practiced otherwise than as described. For example, the fixation mechanism may be provided on the core, on the sleeve or on the core and on the sleeve. The descriptions above are intended to be illustrative, not limiting. However, it will be appreciated that apart from the fixation mechanism the modular applicator according to a particular embodiment may consist of one core and one sleeve in use. The sleeve may be selectable from a set of suitable sleeves. Thus, it will be apparent to one skilled in the art that modifications may be made to the invention as described in the foregoing without departing from the scope of the claims set out below.

We claim:

1. A modular brachytherapy applicator for insertion into a cavity of a patient for administering a radioactive treatment, the applicator comprising:
   a central core, wherein the core includes a connector portion for attaching a catheter to the core to receive the radioactive treatment;

an outer sleeve dimensioned for insertion into the cavity of the patient, wherein the sleeve comprises:
a body having a proximal end and a distal end;
an opening located in the proximal end configured to receive the core; and
a hollow, interior region dimensioned to receive a majority of the core within a majority of the hollow, interior region of the sleeve for removably mounting the sleeve on the core via the opening in the proximal end of the sleeve, wherein the hollow, interior region extends along a majority of a length of the sleeve from the opening in the proximal end to a distal region;
an exterior surface configured to contact the cavity of the patient; and
a fixation mechanism located on the sleeve,
wherein the fixation mechanism includes a portion of the sleeve that is configured to interact with a portion of the core to secure the core within the sleeve at a location along a length of the core and to retain the sleeve on the core when the core is received within the sleeve,
wherein the fixation mechanism is configured to permit movement of the sleeve along the length of the core when the core is received within the sleeve,
wherein the distal end of the sleeve is configured to be adjustable in response to movement of the sleeve along the length of the core, and
wherein the core is configured to be interchangeably received within a plurality of different sleeves.

2. The applicator according to claim 1, wherein a cross-sectional shape of the exterior surface of the sleeve varies along the length of the sleeve.

3. The applicator according to claim 1, wherein a cross-sectional width of the exterior surface of the sleeve varies along the length of the sleeve.

4. The applicator according to claim 1, wherein the core is configured to be interchangeably received within a plurality of different sleeves, the exterior surface of each of the plurality of different sleeves having a different shape.

5. The applicator according to claim 1, wherein the core has a fixed shape and size.

6. The applicator according to claim 1, wherein the sleeve is formed of a substantially rigid material.

7. The applicator according to claim 1, wherein at least a portion of the sleeve is configured to conform to the cavity of the patient when placed within the cavity of the patient.

8. The applicator according to claim 7, wherein the sleeve is formed of a settable polymer and is configured to cure within the cavity of the patient.

9. The applicator according to claim 7, wherein the sleeve is formed of a foam and is configured to harden within the cavity of the patient.

10. The applicator according to claim 1, wherein at least a portion of the exterior surface of the sleeve is textured.

11. The applicator according to claim 1, wherein the sleeve is formed of a transparent material.

12. The applicator according to claim 1, wherein the sleeve is flexible.

13. The applicator of claim 12, wherein the sleeve includes a plurality of segments, wherein at least some of the segments are moveable relative to each other.

14. The applicator of claim 13, wherein at least some of the segments are pivotable relative to each other.

15. The applicator according to claim 13, wherein at least some of the segments are laterally displaceable relative to each other.

16. The applicator according to claim 13 further comprising an indicator for indicating an amount of relative movement of the segments.

17. The applicator according to claim 1, wherein the fixation mechanism includes at least one of a snap fit mechanism, a rotational fit mechanism, a bayonet-type mechanism, a lock, or a fastening clamp.

18. The applicator according to claim 1, wherein the core includes a lumen extending along a length of the core, wherein the lumen is dimensioned to receive a conduit for delivering the radioactive treatment to the cavity of the patient.

19. The applicator according to claim 18, wherein the conduit is an inter-uterine tube.

20. The applicator according to claim 18, wherein the distal end of the sleeve includes a hole dimensioned to allow the conduit to extend from the core to a region exterior of the sleeve.

21. The applicator according to claim 20, wherein the applicator is configured so that when the core is received within the sleeve, and the conduit is received within the core, a length of extension of the conduit from the hole in the distal end of the sleeve is adjustable.

22. The applicator according to claim 1, wherein the core comprises:
a proximal end and a distal end, wherein a majority of the core extending from the distal end to the proximal end is dimensioned to be removably received within the sleeve of the applicator, and wherein the connector portion is located at the proximal end of the core and is dimensioned to couple with a delivery device to receive the radioactive treatment from the delivery device; and
at least one lumen for containing the radioactive treatment received from the delivery device;
wherein the core is configured to adjust the distal end of the sleeve in response to movement of the sleeve along the length of the core, and
wherein the core is configured to be interchangeably received within the plurality of different sleeves to form the modular brachytherapy applicator, wherein the modular brachytherapy applicator is capable of having a plurality of different shapes depending on which of the plurality of different sleeves the core is received within.

23. The applicator of claim 22, wherein a first lumen of the at least one lumen houses an inter-uterine tube.

24. A modular brachytherapy applicator for insertion into a cavity of a patient for administering a radioactive treatment, the applicator comprising:
a central core, wherein the core includes a connector portion dimensioned to couple with a delivery device to receive the radioactive treatment from the delivery device, and wherein the core includes at least one lumen extending along a length of the core for containing the radioactive treatment received from the delivery device;
an outer sleeve having a proximal end and a distal end and a body dimensioned for being inserted into the cavity of the patient, wherein the sleeve comprises:
an opening located in the proximal end;
a hollow, interior region extending from the opening to a distal region, wherein the hollow interior region extends along a majority of a length of the sleeve, and wherein the hollow, interior region is dimensioned to receive a majority of the core within a majority of the sleeve for removably mounting the sleeve on the core;

an exterior surface configured to contact the cavity of the patient; and a fixation mechanism located on the sleeve, wherein the fixation mechanism includes a portion of the sleeve that interacts with a portion of the core to secure the core within the sleeve at a location along the length of the core and to retain the sleeve on the core when the core is received within the sleeve, and wherein the fixation mechanism is configured to permit movement of the sleeve along the length of the core when the core is received within the sleeve, wherein the distal end of the sleeve is configured to be adjustable in response to movement of the sleeve along the length of the core, and wherein the core is configured to be interchangeably received within a plurality of different sleeves.

25. The applicator according to claim 24, wherein the fixation mechanism includes at least one of a snap fit mechanism, a rotational fit mechanism, a bayonet-type fit mechanism, a lock fit mechanism, or a fastening clamp mechanism.

26. The applicator according to claim 24, wherein the at least one lumen houses an inter-uterine tube for containing the radioactive treatment received from the delivery device.

27. The applicator according to claim 26, wherein the inter-uterine tube projects from a hole located in one end of the sleeve when the core is received within the sleeve.

28. The applicator according to claim 24, wherein the connector portion couples with the delivery device using at least one of a catheter cap or a fixation nut.

29. The applicator of claim 24, wherein the sleeve is formed as a single unitary structure.

30. An outer sleeve of a modular brachytherapy applicator configured for insertion into a cavity of a patient for administering radioactive treatment, the sleeve comprising:

a body having a proximal end and a distal end, wherein the body of the sleeve is dimensioned for insertion into the cavity of the patient;

an opening located in the proximal end;

a hollow, interior region extending from the opening to a distal region, wherein the hollow, interior region extends along a majority of a length of the sleeve, and wherein the hollow, interior region is dimensioned to removably receive a central core of the modular brachytherapy applicator within the hollow, interior region so that the sleeve is configured to receive a majority of the central core within it;

an exterior surface configured to contact the cavity of the patient; and a fixation mechanism located on the sleeve, wherein the fixation mechanism includes a portion of the sleeve that interacts with a portion of the core to secure the core within the sleeve at a location along the length of the core and to retain the sleeve on the core when the core is received within the sleeve, wherein the fixation mechanism is configured to permit movement of the sleeve along the length of the core when the core is received within the sleeve, and wherein the distal end of the sleeve is configured to be adjustable in response to movement of the sleeve along the length of the core.

31. The sleeve of claim 30, further comprising a plurality of segments, wherein the plurality of segments are moveable relative to each other.

32. The sleeve of claim 30, wherein the fixation mechanism includes at least one of a snap fit mechanism, a rotational fit mechanism, a bayonet-type mechanism, a lock, or a fastening clamp.

33. The sleeve of claim 30, wherein a cross-sectional shape of the exterior surface of the sleeve varies along the length of the sleeve.

34. The sleeve of claim 30, wherein a cross-sectional width of the exterior surface of the sleeve varies along the length of the sleeve.

35. The sleeve of claim 30, wherein the sleeve is formed as a single unitary structure.

* * * * *